United States Patent [19]

Hauldren

[11] 4,020,688
[45] May 3, 1977

[54] ULTRASONIC INSPECTION APPARATUS FOR VERTICAL MEMBERS

[75] Inventor: H. Morris Hauldren, Culloden, W. Va.

[73] Assignee: W. C. Lamb, Lafayette, La.

[22] Filed: Oct. 8, 1975

[21] Appl. No.: 620,748

[52] U.S. Cl. .............................. 73/151; 73/67.8 S
[51] Int. Cl.² .......................................... G01N 29/04
[58] Field of Search ............ 73/151, 67.8 S, 67.8 R, 73/67.7, 67.5 R, 67.6

[56] References Cited

UNITED STATES PATENTS

| | | | |
|---|---|---|---|
| 3,248,933 | 5/1966 | Stebbins | 73/67.8 S X |
| 3,540,266 | 11/1970 | Lofgren | 73/67.8 S |
| 3,575,043 | 4/1971 | Allen | 73/67.8 S |

*Primary Examiner*—Jerry W. Myracle
*Attorney, Agent, or Firm*—Arnold, White & Durkee

[57] ABSTRACT

An ultrasonic inspection apparatus for use in inspecting drill pipe or like tubular members being tripped into and out of a well borehole comprises a planarly arranged set of ultrasonic search units, such as wheel search units, arranged on a frame suspendible within the well derrick and defining a vertical passage for the tubular member. Access is provided to the passage by the tubular member from a direction transverse to the longitudinal axis of the tubular member, for example, by providing an openable hinged frame. When in the passage, the search units are urged into contact with and are sonically coupled to the tubular member. The device is manually manipulable to engage and disengage the tubular member to facilitate inspection. A method of inspecting tubular goods on the floor of a drilling rig during a tripping operation is also provided.

26 Claims, 5 Drawing Figures

ULTRASONIC INSPECTION APPARATUS FOR VERTICAL MEMBERS

IDENTIFICATION OF RELATED APPLICATIONS

This application is related in subject matter to co-pending U.S. application Ser. No. 620,747, entitled "Ultrasonic Inspection Apparatus for Well Operations" filed on even date herewith in the names of H. Morris Hauldren, Jack C. Claycomb, Deke E. Dekerlegand, and Chi-Haung Chang, and commonly assigned with this application.

BACKGROUND AND PRIOR ART

This invention relates to a device for the nondestructive ultrasonic testing of tubular goods for detection of small internal cracks and other types of discontinuities or imperfections. More specifically, the instant invention provides a novel apparatus for conducting the inspection of tubular goods employed in the drilling of oil and gas wells while such tubular goods are being passed out of or into the well borehole during a drilling operation. The device of the instant invention permits on-site inspection of the drill pipe employed in the drilling operation or well casing or tubing while it is being set, and is particularly useful since it enables inspection of the pipe as it is being tripped into the borehole, and consequently, permits ready identification of flawed tubular goods which might produce drilling string failures if used when drilling is recommenced.

The use of ultrasonic testing techniques, and specifically of ultrasonic crystals, for detecting discontinuities in metal products is a common mode of nondestructive testing. The crystals employed are typically piezoelectric crystals made of a material such as quartz. These crystals produce ultrasonic vibrations in response to a voltage of appropriate frequency impressed upon the crystal. When inspecting a tubular product for internal flaws using a reflection method, the crystal is maintained in a position relative to the surface of the product to transmit a short duration sonic wave pulse into the product at an angle such that a defect or discontinuity will cause the waves to be reflected to the crystal and produced a voltage response in the crystal. Since the crystal is de-energized immediately following the pulsed emission of a wave, reflected waves are received during de-energized periods and hence the reflected waves will produce a discernible signal which may be monitored, for example, on a cathode ray tube or a strip chart recorder. Pulse repetition rates of between 60 and 2000 pulses per second are employed for various types of inspections.

Typically, an ultrasonic inspection device will be calibrated using a standard identical to the goods being inspected. The standard may have one or more discontinuities of known magnitude so that the response of the device to known imperfections may be ascertained, and standards for accepting or rejecting the inspected goods may be established.

Ultrasonic inspection techniques are most typically employed at the site of manufacture of the articles being inspected. Thus, plate or tubular goods are typically inspected at the manufacturing plant using techniques which are well known in the art. However, the on-site inspection of tubular goods presents different and unique problems.

In well drilling operations, drill pipe failure can be a costly and time-consuming occurrence. Washouts or drill string breakage can occur frequently if drill pipe with sufficiently serious imperfections is employed. Most frequently such failures result from internal flaws in the tubular goods being used. Confronted with such a failure, it becomes necessary to trip the pipe out of the borehole to replace the failed joint. In the case of drill string breakage, it is also necessary to fish the parted portion of the string from the borehole before drilling can be recommenced. Hence, the value of an efficacious method of inspection, particularly for internal flaws in drill pipe is obvious.

During drilling operations, the drill string is frequently tripped into and out of the borehole to replace a worn drill bit, to set casing at various levels or to conduct other operations. During these trips, it is preferred to stack the drill pipe vertically within the well derrick rather than transporting it from the elevated rig floor to racks maintained at ground level. In offshore drilling operations, it is also common to stack drill pipe vertically. Inspection of a drilling string is desirably conducted periodically, e.g., every two or three months, to detect the existence of flaws in drill pipe which would render the pipe susceptible to failure in subsequent drilling operations. Hence, to provide most efficient inspection of tubular goods in well drilling operations, it is necessary to provide an inspection device which can inspect tubular goods in a vertical portion in the well derrick. With such a device inspections could be conducted during a tripping operation made necessary by factors such as a replacement of a worn drill bit. Furthermore, since it is necessary to join individual stands of pipe (comprising typically two or three pipe joints or sections) at the rig floor level when assembling a drilling string, it is necessary that a useful inspection device be readily engaged and disengaged from about the pipe being inspected.

SUMMARY OF THE INVENTION

In accordance with the instant invention, there is provided a device for nondestructive ultrasonic inspection of tubular goods disposed in a substantially vertical position. Specifically, the instant invention provides a device which may be used on site at a well derrick to inspect drill pipe, casing or tubing, while these tubular members are being tripped into and out of a well borehole.

The instant invention also provides a novel method of inspecting tubular goods while they are being tripped into or out of a well borehole. In a particular embodiment, the instant invention provides a method for inspecting tubular goods being tripped out of a borehole for imperfections transverse to the longitudinal axis.

When a pipe is being tripped out of a borehole, the surface of the pipe is typically covered with drilling mud and drilling debris. Moreover, there may exist liquid films flowing on the interior of the pipe as the pipe is withdrawn from a liquid-filled borehole. The existence of drilling mud or debris on the exterior of the pipe can create coupling difficulties with an ultrasonic inspection device. Moreover, liquid films flowing down a pipe can create false "reflections" which would mask the existence of discontinuities of flaws which are sought to be detected, or give false indications of the existence of such imperfections. Accordingly, unless a drill pipe can be substantially cleaned during its withdrawal from the borehole, the device of the instant invention will be more typically employed to conduct the ultrasonic inspection during a pipe tripping operation into the borehole.

In accordance with this invention, there is provided an apparatus for ultrasonic inspection of substantially vertically disposed tubular members which comprises a frame that may be disposed around the tubular member while in vertical position, and ultrasonic transducers which are urged against the tubular member when the frame is disposed around the pipe. The provision of such a removable frame adapted to accept and discharge the pipe in a direction transverse to the axis of the pipe enables the inspection to be conducted, for example, when tripping pipe in and out of a borehole. If a discontinuity or imperfection in the pipe is detected, the tripping operation is stopped, the ultrasonic inspection device is withdrawn from the pipe and the joint of pipe containing the flaw may be removed from the drilling string. When the string is reassembled, the ultrasonic inspection device may be readily replaced in inspecting position around the pipe to continue monitoring of the pipe as it passes into the borehole.

Specifically, the apparatus of the instant invention comprises a frame defining a vertical passage for the tubular member to be inspected. The frame provides access of tubular member to the vertical passage from a direction transverse to the axis of the tubular member. Thus, for example, the frame may be hinged to swing open for accepting the pipe transversely into the vertical passage through the frame. Alternatively, the frame may have an opening to provide access of the pipe transversely to the vertical passage, and further include means to urge ultrasonic search units into a sonically coupled relationship with the pipe. In accordance with this invention, the ultrasonic inspection device is employed to detect flaws which are transverse to the longitudinal axis of the tubular member. In such an arrangement, the search units emit a sonic wave which is coupled to the tubular member at an acute angle to the longitudinal axis of the member. Sufficient ultrasonic devices are arranged about the pipe in order that the combined beam spread of the search units will survey the entire circumference of the tubular member.

A plurality of ultrasonic search units are mounted in the frame of the apparatus. These search units comprise rolling wheels having a flexible surface, in the nature of an inflated tire, adapted to conform to the shape of the tubular member. The surface material is generally transparent to the ultrasonic signal. Each search unit includes within the wheel a piezoelectric type crystal and a coupling agent to transmit the sonic signal from the crystal to the flexible material comprising the wheel surface. A further coupling agent, such as water is then injected between the flexible surface of the rolling wheel and the tubular member in order to assure transmission of the sonic signal from the rolling wheel into the wall of the tubular member being inspected. Springs or like biasing means are disposed to urge each of the ultrasonic transducer wheels against the tubular member while in the vertical passage. The springs are so arranged to enable the rolling wheels to overcome tool joints or like raised portions on the tubular members as they are advanced through the inspection device.

The frame of the inspection device also supports an ultrasonic inspection instrument comprising a pulser/receiver to energize the piezoelectric crystals within the ultrasonic search units and also to detect reflected waves. The instrument also includes a display in the form of a cathode ray tube, a strip chart recorder or the like to produce a readable response to reflected waves indicating the presence of discontinuities. An audible indication of the existence of discontinuities might alternatively be provided. The entire apparatus may be advantageously suspended from an overhead line in the well derrick from a point proximate the center of gravity of the apparatus thus facilitating the manual manipulation of the device into and out of engagement with the tubular goods being inspected.

Further, in accordance with this invention, a single pulser unit is used to pulse all the search units, and a single display or other indication is produced from the combined responses of the search units to reflected waves indicative of discontinuities. Thus, a device operable by one man on the derrick floor is provided.

In accordance with the instant invention, there is also provided a novel method for inspection of tubular members used in well drilling operations on the platform of a well derrick while the tubular members are being tripped into and out of a well borehole. In accordance with this method, the tubular member is suspended over the well borehole during the insertion or withdrawal operation using an elevator or the like. A plurality of ultrasonic search units, preferably wheel search units containing electro-acoustical transducers such as piezoelectric crystals, are placed in contact with the pipe and are sonically coupled to the pipe with a suitable couplant such as water. The search units are preferably maintained in a single horizontal plane. The tubular member is then moved into or out of the borehole and the search units are simultaneously and repetitively pulsed to transmit ultrasonic signals into the well of the tubular member. These ultrasonic signals are transmitted at an angle acute to the longitudinal axis of the member and are directed to advance longitudinally down the tubular member, preferably in a direction generally parallel to the longitudinal axis of the tubular member. As the signal beams advance from the search unit, they tend to spread. In order to be assured that the inspection procedure will detect all discontinuities, sufficient search units to obtain a beam spread which will survey the entire circumference of the tubular member at a longitudinal distance from search units where discontinuities desired to be detected will produce an effective and discernible response. Generally, three and preferably four wheel search units are employed, although more may be required for large diameter tubular members.

Reflected ultrasonic signals from discontinuities within the tubular member are detected by the same search units, during periods when the electro-acoustic transducers are de-energized. The transducers produce an electrical signal which is then transmitted to a suitable indicator device to produce a sensible indication, e.g., an audible or visual indication of a discontinuity. Most typically, a display device such as the cathode ray tube of an oscilloscope or a strip chart recorder is employed. Preferably, a single pulser/receiver unit is employed. A junction block which is suitably impedance matched to the transmission lines between the pulser/receiver and the individual search units combines the electrical signals corresponding to reflections from discontinuities from the search units to a single display output.

BREIF DESCRIPTION OF THE DRAWINGS

This invention will further be illustrated by reference to the appended drawings which illustrate a particular embodiment of the ultrasonic inspection device in accordance with this invention.

DESCRIPTION OF THE SPECIFIC AND PREFERRED EMBODIMENTS

Figure 1:
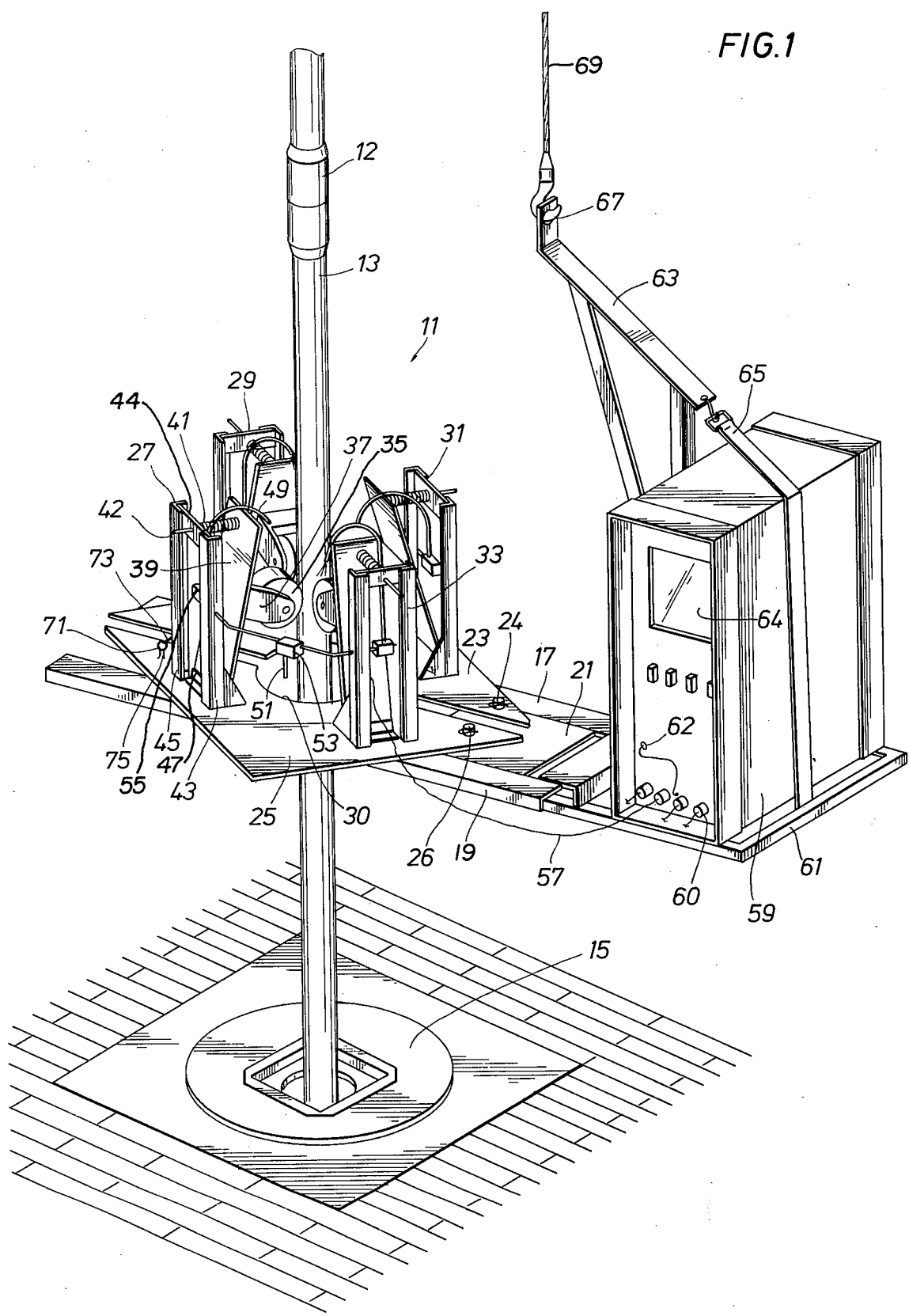
FIG. 1 is a perspective view of an ultrasonic inspection device in accordance with this invention shown in place on a drill pipe and disposed over the rotary table on a drilling platform.
Figure 2:
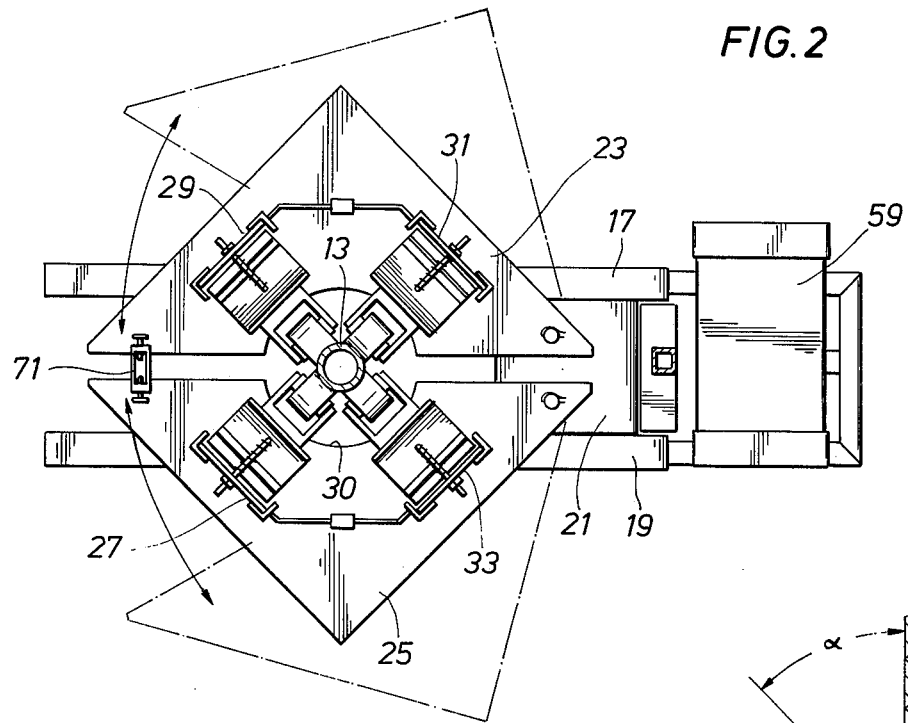
FIG. 2 is a top view of the ultrasonic inspection device illustrated in FIG. 1.

Referring now to FIG. 1, there is shown in perspective view an ultrasonic inspection apparatus 11 in accordance with this invention in position around a pipe 13 disposed through the rotary table opening on a drilling rig floor 15. Pipe 13 is joined at joint 12 with other joints of pipe and is suspended in a well derrick (not shown) by means of an elevator or like device (not shown). The ultrasonic inspection device comprises a frame having two generally parallel horizontally disposed supports 17 and 19 spanned by and rigidly affixed to brace 21. Two base plates, 23 and 25, are pinned for pivotal movement in a plane parallel to the supports at points 24 and 26. As shown in the top view of FIG. 2, an opening in base plates 23 and 25 in the center portion thereof defines a central vertical passage 30 in the apparatus which can accommodate the tubular member being inspected. Latch 71, disposed proximate the nonpivoted end of the plates 23 and 25 may comprise a hook on plate 23 adapted to engage eye on plate 25 or any other suitable device to maintain the plates in closed position around the pipe 13.

Each base plate supports two transducer brackets in the configuration shown. Specifically, base plate 23 supports transducer brackets 29 and 31, while base plate 25 supports transducer brackets 27 and 33. The brackets are disposed around the central opening 30 to support search units in 90-degree centers around the pipe being inspected as will be explained below. Each of the transducer brackets is identical in construction, and hence the description shall be in reference to transducer bracket 27.

It will be understood that in accordance with this invention, any desired number of ultrasonic search units may be used to effect the pipe inspection. The illustrated embodiment shows four such search units arranged in the same horizontal plane around the pipe on 90-degree centers. However, it may be satisfactory depending upon the size of the pipe and the beam spread of the electro-acoustical transducers employed within the search units to utilize more or less ultrasonic search units when scanning the pipe for imperfections or discontinuities transverse to the axis of the tubular member being inspected. Most often at least three search units will be employed. With large diameter tubular members, however, it may be necessary to use additional search units to obtain the necessary beam coverage. As indicated hereinabove, it is sufficient so long as the beam spread of the search units permits an effective survey of the entire circumference of the pipe as it passes through the apparatus.

Figure 3:
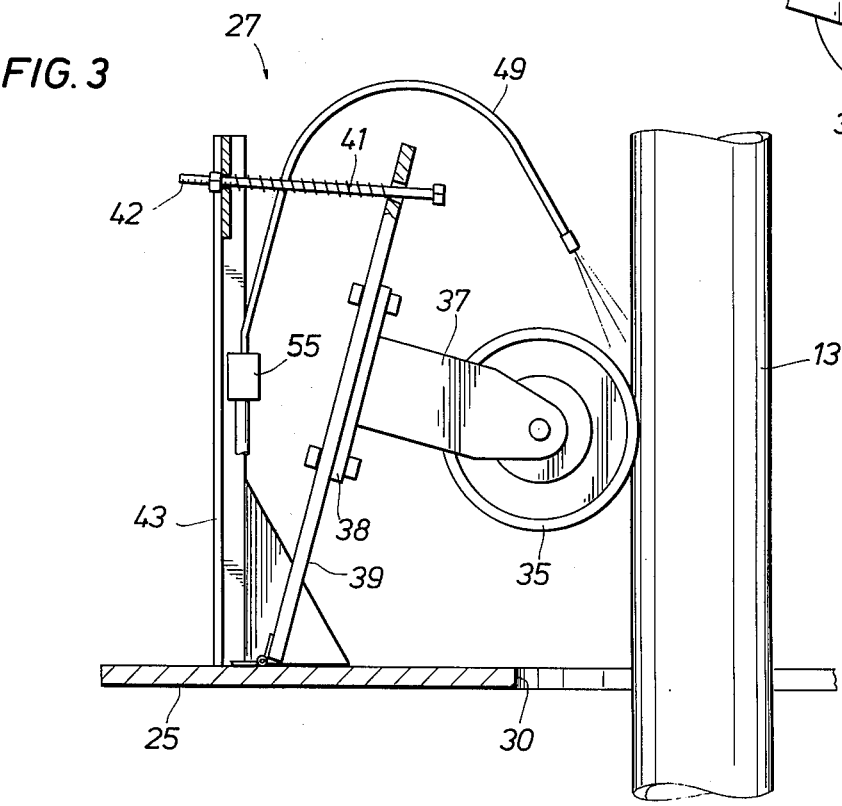
FIG. 3 is a side view of an ultrasonic transducer device employed in the inspection apparatus of FIG. 1, specifically showing a rolling wheel in contact with the pipe and showing means urging the wheel into engagement with the tubular member being inspected.

Bracket 27, illustrated in FIG. 1 and shown in side elevation in FIG. 3, is composed of two vertical members 43 and 45 and cross brace 44 affixed therebetween. Bracket 27 is fixed to base plate 25 for example by welding or the like. Alternatively, the brackets may be bolted in place on base plate 24 as will be appreciated by those skilled in the art.

Mounting plate 39 is hinged to base plate 25 by hinge 47 and is biased away from cross brace 44 by means of spring 41. Adjustment screw 42 enables adjustment of the angular disposition of mounting plate 39 to accommodate pipe of different diameter. The wheel search unit comprising base plate 38, bracket 37, and wheel 35 is affixed to mounting plate 39, for example, by means of bolts. The search unit employed in the device of this invention is preferably a variable angle beam wheel search unit housing an electro-acoustical transducer such as a piezoelectric crystal of a type well known in the art. Such wheel search units are manufactured by Sperry Division of Automation Industries, Inc. and have been sold under Nos. 50C481 and 50C541.

Preferably, in order to scan for discontinuities transverse to the longitudinal axis of a tubular member, the wheel search unit maintains the piezoelectric crystal disposed at an angle approximately 45 degrees to the axis of the tubular member being inspected and oriented to direct a longitudinal sonic beam generally longitudinally along the inner pipe wall. The optimal angle may vary slightly depending upon the size and wall thickness of the pipe being inspected. For example, on some pipe having a diameter between 3½ and 4½ inches, it has been found that an attack angle of the sonic beam from the piezoelectric cyrstal is optimal at an angle of 43½° to the longitudinal axis of the pipe. However, in determining the optimal disposition of the piezoelectric crystal, it is preferred to initially calibrate the unit with a standard test pipe section having a discontinuity of known dimension. The unit is activated and the angle of attack of the piezoelectric crystal is adjusted until the known discontinuity gives the maximum electrical response on the ultrasonic inspection instruments, which will be described hereinbelow. Commercially available wheel search units have variable angle crystals enabling adjustment of the angle of attack of the piezoelectric crystal with respect to the member being inspected. Use of such variable angle beam wheel search units with the illustrated embodiment is preferred.

The wheel search unit is typically comprised of a flexible tirelike wheel 35 which is transparent to the ultrasonic signal, mounted for rotation about an axis supported by bracket 37. A piezoelectric crystal is mounted on a nonrotating axle within the wheel. Three common types of piezoelectric materials are quartz, lithium sulfate and polarized ceramics. The flexible tire 35 is then filled with a suitable coupling or other type agent which search units could be employed. Shoe type search units which are dragged over the pipe surface or other search units not using a rotating sheel are not preferred under the rugged conditions of a drilling rig but may be used. Coupling agents which have been used in the art include glycols or glycol ethers, for example, the Cellusolve products sold by Union Carbide Corporation. In order to accomplish coupling between the flexible tire 35 and the tubular member 13 being inspected, it is preferred to provide a liquid coupling agent on the surface of the pipe. Accordingly, water lines such as 49 are provided above each wheel search unit and provide a constant stream of water to create a uniform film between flexible tire 35 and the pipe being inspected to serve as a sonic coupling agent. Tube 49 is fed through manifolds 55 and 53 and water transport line 51 which is connected to a suitable water supply. A gravity flow of water is satisfactory to provide a coupling agent to the search units, although a pumped source may also be employed. It is most desirable that the coupling agent form a film between the surface of the wheel and the tubular member and hence high velocities which would cause creation of bubbles should be avoided when supplying the coupling agent to the wheel surface. It will be understood by those skilled in the art that other coupling agents may be used rather than water during operation of the device. However, water operates satisfactorily and is clearly the most available and least expensive coupling agent to be used on the exterior of the pipe being inspected.

Opposite the search units on the support frame, there extends platform 61 of suitable size and dimension to support an ultrasonic inspection instrument 59. Illustrated ultrasonic inspection instrument 59 includes a pulse generator and receiver unit as well as a cathode ray tube for display purposes. Such ultrasonic search instruments are well known in the art. For example, Sperry Division of Automation Industries offers a 10M pulser/receiver unit packaged with a type UN, style 50E533 oscilloscope which may be used with the inspection device in accordance with the invention. Similar battery-operated pulser/receivers having cathode ray displays are currently available and may be used. In addition, it is pointed out that a permanent recorder may be used in place of or in addition to the cathode ray tube display.

Figure 5:
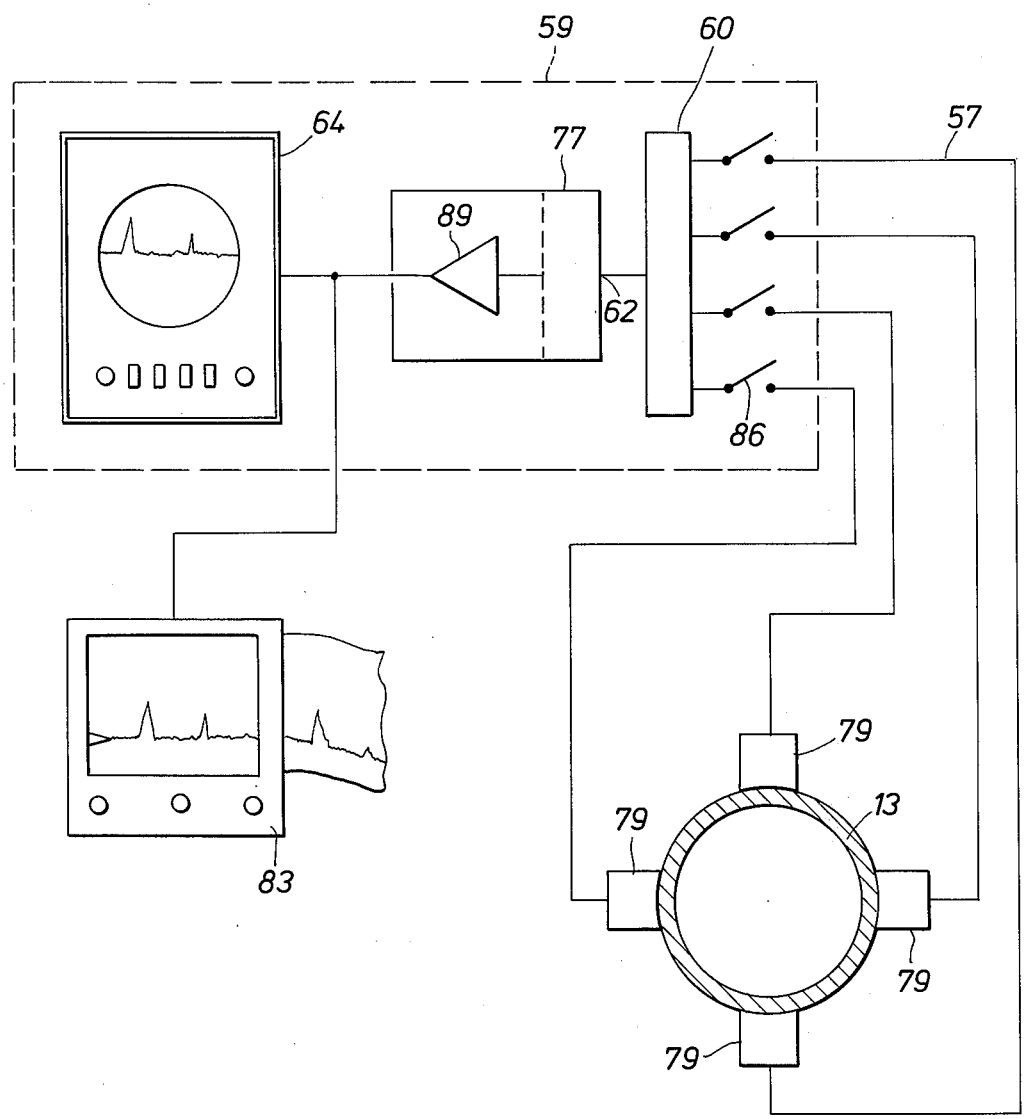
FIG. 5 is a schematic illustration of the ultrasonic inspection apparatus and associated peripheral devices for displaying and recording inspection runs.

Referring to FIG. 5, the pulser/receiver 77 within instrument 59 generates a series of pulses which are simultaneously transmitted to piezoelectric crystals 79 in each of the wheel search units 35 through transmission lines 57 exiting junction block 60 with all switches 86 in closed position. Typically available search instruments provide only a single pulse output on the pulser/receiver. Junction block 60 merely divides the signal to the four transmission lines and contains means for impedence matching the transmission lines and hence optimally tuning the signal transmitted to each wheel search unit. Such impedance matching techniques are well known in the art, and may include a suitable RC circuit or a resistor-inductor combination.

Figure 4:
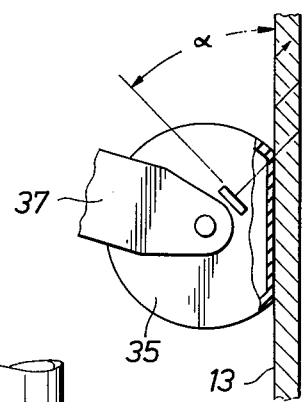
FIG. 4 is a schematic illustration of the disposition of a piezoelectric type crystal within the ultrasonic transducer wheel in accordance with this invention illustrating the angular disposition of the crystal with respect to the tubular member being inspected.

When the piezoelectric crystals are energized, they transmit a sonic beam at an acute angle $\alpha$ into the tubular member being inspected as schematically shown in FIG. 4. The wave is reflected between the opposing walls of the tubular member and progresses longitudinally. If the beam encounters a discontinuity, a reflected signal will return and be picked up by the piezoelectric crystal. As set forth above, angle $\alpha$ is usually about 45° though this may be varied depending upon the material being inspected and the type of discontinuity that is sought to be detected. Switches 86 (which would be incorporated within instrument 59) enable the operator to activate and monitor each search unit individually or in any combination. During periods when the piezoelectric crystals are de-energized, reflected signals from discontinuities sensed within the pipe are transmitted through transmission lines 57 and through junction block 60 to provide a single output signal at jack 62 of the pulser/receiver portion 77 of instrument 59. For optimal transmission lines 57 are cut to lengths which correspond to multiples of the quarter wave length of the signal. The signal is amplified in the amplifier 89 within pulser/receiver portion 77 of instrument 59 and displayed on oscilloscope 64 and/or recorded on a strip chart recorder 83.

The frequency of the signal to energize the crystals employed in connection with inspection operations using the apparatus of this invention may vary as will be understood by those skilled in the art. Typical inspection operations may be conducted using signals having frequencies of 1 megacycle to 5 megacycles. Eminently successful inspections have been conducted on drill pipe utilizing a frequency of 2.25 megacycles. The pulse repetition rate may vary between 60 and 2000 pulses per second as is known in the art. Pulse duration is in the microsecond range, for example, between 1 and 5 microseconds.

Instrument 59 is retained on platform 61 by means of a strap 65 which is engaged at its upper end by a hook extending from support 63. Support 63 terminates in an eye 67 which may be engaged to an overhead line 69 on the well derrick. Eye 57 is desirably provided over the center of gravity of the entire apparatus so that during use, minimal lateral forces are imposed upon the search units engaging the tubular member being inspected.

Accordingly, when the apparatus in accordance with this invention is to be used, the unit is manipulated over the rotary table on line 69, latch 71 is opened and plates 23 and 25 are pivoted outwardly to enable the pipe 13 to be received between supports 17 and 19. The device is manually manipulated until pipe 13 is disposed centrally between the supports, and plates 23 and 25 are swung back to their original positions and latched in place with latch 71. Springs 41 will then urge each wheel search unit into engagement with the tubular member, and the passage of the pipe into the borehole commences, with the inspection unit being maintained in generally fixed position.

Water flow is then commenced from tubes 49 to couple the wheel search units to the pipe. The pulser portion of instrument 59 is activated and the four wheel search units simultaneously transmit a pulse into the tubular member. The pulse is preferably directed upwardly away from the rotary table at an acute angle to the longitudinal axis of the tubular member. The receiver portion of the instrument detects reflected signals and displays the result on the oscilloscope 64.

When the inspection apparatus 11 encounters tool joint 12, the biasing springs will yield permitting the search units to ride over the raised tool joint. When a serious discontinuity is detected in oscilloscope 64, latch 71 is loosed and the apparatus is manually removed from the tubular member. The faulty section is then removed, the string reconnected and the inspection device is repositioned to resume the inspection operation.

The instant invention has been disclosed in connection with specific embodiments. However, it will be apparent to those skilled in the art that variations from the illustrated embodiment may be undertaken without departing from the spirit or scope of the invention. For example, separate displays may be provided for different search units or combinations of search units. The coplanar relation of the search units need not be adhered to since each unit can be individually monitored using switches 86, and in dealing with small diameter tubing, such may be desirable. As a further alternative, the search units may be biased into sonically coupled relation with the tubular member using a hydraulic system. A limit switch might be installed to detect an advancing tool joint and withdraw the search units from contact with the tubular member. These and other variations will be obvious to those of skill in the art and are within the spirit and scope of this invention.

What is claimed is:

1. Apparatus for ultrasonic inspection of a substantially vertically disposed tubular member which comprises:
   a frame having a horizontally extending baseplate with an opening therein defining a vertical passage for the tubular member to move through relative to the baseplate,
   said frame providing access of said tubular member to said passage from a direction transverse to the longitudinal axis of said tubular member;
   a plurality of ultrasonic search units mounted on said frame in spaced relation relative to the circumference of said member, each of said ultrasonic search units comprising a wheel disposed in rolling contact with said tubular member,
   each of said wheels including an electroacoustic transducer sonically coupled to said tubular member; and
   means urging said wheels against the tubular member disposed in said passage.

2. The apparatus of claim 1, wherein said plurality of ultrasonic search units are disposed in substantially the same plane.

3. The apparatus of claim 1, wherein said wheels are disposed to roll along a path parallel to the longitudinal axis of said tubular member.

4. The apparatus of claim 1, wherin said means urging said wheels into contact with said tubular member is yieldable to permit said wheels to roll over outer protrusions on said tubular member.

5. The apparatus of claim 1, wherein said plurality of ultrasonic search wheels are sonically coupled with a liquid film formed between said wheels and said tubular member by liquid injection.

6. The apparatus of claim 1, wherein said electroacoustic transducers are simultaneously energized from a common source.

7. The apparatus of claim 1, wherein said electroacoustic transducers are piezoelectric crystals.

8. The apparatus of claim 1, wherein each of said electroacoustic transducers is disposed within its respective wheel at an angle of 43½° with the longitudinal axis of the tubular member.

9. The apparatus of claim 1, wherein said electroacoustic transducers are disposed within said wheels to project a sonic beam upwardly and into said tubular member.

10. The apparatus of claim 1, wherein said electroacoustic transducers produce electrical signals in response to sonic waves reflected from discontinuities within said tubular member, said electrical signals being combined to form a single signal indicative of the presence of discontinuities within said tubular member.

11. The apparatus of claim 10, further comprising a display device for visually displaying said single signal.

12. The apparatus of claim 11, wherein said display device is a cathode ray tube instrument.

13. The apparatus of claim 11, wherein said display device is a strip chart recorder.

14. Apparatus for ultrasonic inspection of a substantially vertical tubular member suspended above the rig floor of a well derrick which comprises:
   a frame defining a vertical passage for the tubular member,
   said frame providing access of said tubular member to said passage from a direction transverse to the tubular member;
   a plurality of ultrasonic search units mounted on said frame in spaced relation around the circumference of the tubular member and maintained in sonically coupled relation with the tubular member, to transmit ultrasonic pulses at an acute angle to the longitudinal axis of said tubular member, and to receive reflected pulses from discontinuities within said tubular member and produce an electrical signal functionally related to said reflected pulses,
   said search units being arranged to jointly produce beam spread of said pulse which covers the full circumference of said tubular member;
   means combining the reflected pulses from said search units to provide a single indication of the existence of a discontinuity within said tubular member.

15. The apparatus of claim 14, wherein said search units comprise a wheel disposed in rolling contact with said tubular member, each of said wheels including an electro-acoustic transducer.

16. The apparatus of claim 15, further comprising means for urging said wheels against said tubular member.

17. The apparatus of claim 14, wherein said ultrasonic search units are disposed in substantially the same plane.

18. The apparatus of claim 14, wherein said signal combining means is a visual display device.

19. The apparatus of claim 14, wherein said frame includes a laterally extending platform for accommodating an ultrasonic inspection instrument.

20. The apparatus of claim 19, further comprising a support attaching to said frame and extending upwardly terminating in a connecting device, said connection device being disposed directly above the center of gravity of the ultrasonic inspection apparatus.

21. A method of inspecting a tubular member used in well drilling operations on a drilling platform of a well derrick while said member is being inserted or retrieved from a well borehole which comprises the steps of:
   vertically suspending said tubular member within the well derrick;
   sonically coupling a plurality of ultrasonic search units to said suspended tubular member;
   moving said tubular member vertically relative to said borehole while maintaining said search units in relatively fixed position;
   simultaneously pulsing said ultrasonic search units to transmit ultrasonic signals into the wall of the tubular member at an angle acute to the longitudinal axis of the tubular member, said combined ultrasonic signals producing a beam spread which covers the full circumference of said tubular member detecting reflected ultrasonic signals from discontinuities within said tubular member with said search units to produce electrical signals functionally related to said reflected ultrasonic signals; and producing a sensible indication responsive to said electrical signals to indicate the presence of a discontinuity within said tubular member.

22. The method of claim 21 wherein said search units are sonically coupled to said tubular member in substantially one horizontal plane.

23. The method of claim 21 wherein said search units are rotatable wheels yieldably urged against said tubular member, and adapted to follow rolling paths parallel to the axis of the tubular member.

24. The method of claim 21 wherein the signals transmitted from said search units into the wall of the tubular member are in a vertical direction away from the borehole.

25. The method of claim 21 including the steps of:
dividing a pulse signal from a single pulse source to said plurality of search units to transmit the ultrasonic signals into the wall of the member, and combining the electrical signals related to said reflected ultrasonic signals to produce a single visible indication of the presence of a discontinuity on a cathode ray tube or a strip chart recorder.

26. A method of inspecting a tubular member used in well drilling operations on a drilling platform of a well derrick while said member is being inserted or retrieved from a well borehole, which comprises the steps of:

vertically suspending said tubular member within the well derrick;

sonically coupling a plurality of ultrasonic rolling wheel search units to said suspended tubular member;

moving said tubular member vertically relative to the borehole, while maintaining said rolling wheel search units in relatively fixed position;

simultaneously pulsing said rolling wheel search units to transmit ultrasonic signals into the wall of the tubular member at an angle acute to the longitudinal axis of the tubular member, said combined ultrasonic signals producing a beam spread which covers the full circumference of said tubular member;

detecting reflected ultrasonic signals from transverse discontinuities within said tubular member with said rolling wheel search unit to produce electrical signals functionally related to the reflected ultrasonic signals;

deriving a single signal from said electrical signals indicative of the presence of a transverse discontinuity within said tubular member; and displaying said single signal to visually indicate the presence of a transverse discontinuity.

* * * * *